United States Patent [19]

Kaye

[11] 4,380,530
[45] Apr. 19, 1983

[54] STERILIZER WITH INFLATABLE ARTICLE HOLDER

[75] Inventor: Saul Kaye, Evanston, Ill.

[73] Assignee: Ben Venue Laboratories, Inc., Bedford, Ohio

[21] Appl. No.: 213,036

[22] Filed: Feb. 13, 1981

[51] Int. Cl.³ .............................................. A61L 2/20
[52] U.S. Cl. ................................. 422/300; 211/60 R; 248/363; 422/297
[58] Field of Search ................ 422/297, 300, 310, 296

[56] References Cited

U.S. PATENT DOCUMENTS

| | | | |
|---|---|---|---|
| 3,163,494 | 12/1964 | Kaye | 422/34 X |
| 3,561,918 | 2/1971 | Ray | 422/34 X |
| 3,598,516 | 8/1971 | Shill et al. | 422/27 |
| 3,963,438 | 6/1976 | Bunez | 422/31 |
| 4,251,482 | 2/1981 | Sanderson et al. | 422/296 X |

FOREIGN PATENT DOCUMENTS 2435037  1/1976  Fed. Rep. of Germany ........ 422/27

OTHER PUBLICATIONS

Pickerill, J. K.; "Practical System for Steam–Formaldehyde Sterilizing"; Lab. Pract. (Great Britain); vol. 124, No. 6, 6/75; pp. 401–404.

Primary Examiner—Barry S. Richman
Attorney, Agent, or Firm—Robert Bruce Henn

[57] ABSTRACT

Apparatus for holding medical and other devices while sterilant gas is passed over and through the device. The apparatus comprises an inflatable cuff which inflates by interior pressure as the pressure in the sterilizer chamber decreases, and relaxes as chamber pressure increases, thereby alternately holding the device and exposing its surfaces to the sterilant gas and desorbing gas.

7 Claims, 9 Drawing Figures

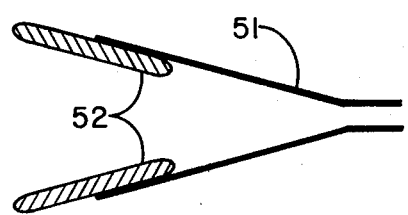
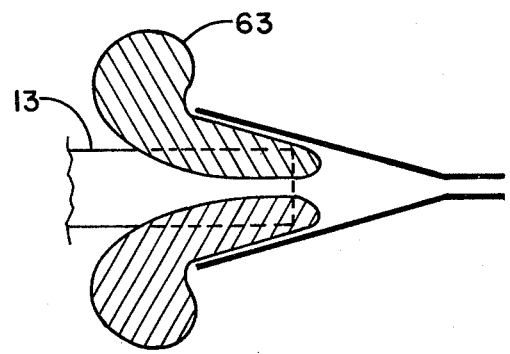
Fig.5  Fig.6
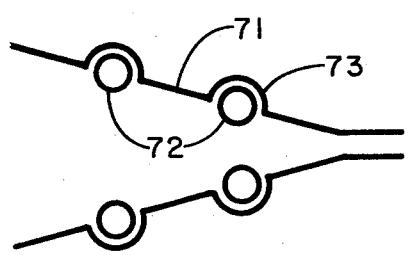
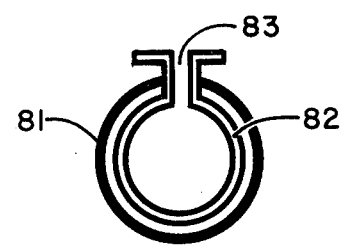
Fig.7  Fig.8
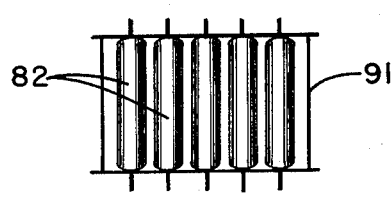
Fig.9

STERILIZER WITH INFLATABLE ARTICLE HOLDER

BACKGROUND OF THE INVENTION

1. Field of the Invention

This invention is in the field of apparatus for holding objects; more particularly, the invention is in the field of deformable apparatus for holding objects by the application of fluid-pressure differential.

2. Description of the Prior Art

Some examples of vapors which may be used to sterilize objects and materials are steam, formaldehyde, and ethylene oxide. It is important not only to generate maximum concentrations of bactericidal chemicals in the vicinity of the surfaces, but also to raise their temperatures to the maximum that can be tolerated in as short a time as possible. This is because the inactivation of micro-organisms is basically a chemical reaction, the speed of which is generally increased in marked fashion by an increase in temperature. In most cases, the configuration of the object being treated assures that the sterilizing atmosphere will contact all surfaces, rendering the entire object sterile. However, even with objects whose contaminated surfaces are readily accessible to the sterilizing atmosphere, a great many precautions must be taken to assure sterilization. These precautions include, e.g., the removal of air from the sterilizer chamber to as great a degree as possible or practical, provision of packaging materials permeable to the sterilizing agent, and arrangement of packaged goods to facilitate contact of sterilizing agent. Such requirements are well known to those skilled in the art of sterilization, and will not be repeated here.

Efforts are made in designing new objects to make it easy for sterilizing vapors to contact, diffuse, permeate or penetrate to, all the internal as well as the external contaminated sites. However, due to their purpose and nature, some medical devices necessarily contain very long and narrow tubules requiring heating and penetration by sterilizing vapors, which must also contact all of the exterior surfaces of the device. Some examples of such devices are catheters and endoscopic instruments.

Some endoscopes contain one or more hollow tubes one millimeter (mm) in diameter and approximately 3600 mm long, whose interiors become contaminated and thus require sterilization. Simply releasing steriliant vapor into a chamber containing a contaminated object of this type does not replace the air contained in the tubule with enough vapor to effect the desired end in a short enough time to be considered practical.

Many sterilizers using vapors have as a preliminary step the removal of much of the chamber air which is then replaced with sterilizing vapor. One such method is described by McDonald in U.S. Pat. No. 3,068,064. However, even this process does not produce, throughout the lumen of the tubule, a high enough concentration of sterilant at a sufficiently high temperature to accomplish the desired end, although the exterior surfaces are effectively sterlized.

SUMMARY OF THE INVENTION

The present invention is a device for holding instruments during sterilization which comprises sealed inflatable means maintained in a rigid holder, the inflatable means being relaxed at ambient pressure, and inflated at reduced exterior pressure.

BRIEF DESCRIPTION OF THE DRAWINGS

FIG. 5 is a view in section of the embodiment of this invention showing a conical configuration.

FIG. 6 shows the embodiment of FIG. 5 in its inflated condition.

FIG. 7 is a sectional view of the holder with a plurality of toroidal elements, set in a conical configuration.

FIG. 8 is a tranverse sectional view of an embodiment showing an inflatable strip maintained in a rigid holder.

FIG. 9 is an end view of a plurality of inflatable strips maintained in a rigid holder.

DESCRIPTION OF THE PREFERRED EMBODIMENTS

The present invention is a device for holding medical instruments and the like during sterilization, which comprises sealed inflatable means maintained in a rigid holder, the inflatable means being in a relaxed, non-rigid state at ambient pressure, and in a rigid or semi-rigid, inflated state under conditions of reduced pressure within gas-tight sterilizing apparatus.

A sterilizer has been devised in which a portion of the chamber atmosphere is continuously removed from the chamber by means of a pump, and returned to it by an external circuit. As is described in my copending application Ser. No. 212,972 dated Feb. 13, 1981, now U.S. Pat. No. 4,337,223 issued June 29, 1982, a minor portion of this recirculated flow is drawn through the entire length of one or more narrow tubules. This guarantees that the tubule surfaces are exposed to the same chamber conditions as are the exterior surfaces of the devices.

In the disclosure of the recirculating sterilizer, one end of each such device is described as being held in a holder or socket connected to the chamber exit port. In the present disclosure, a superior type of holder is described.

Figure 1:
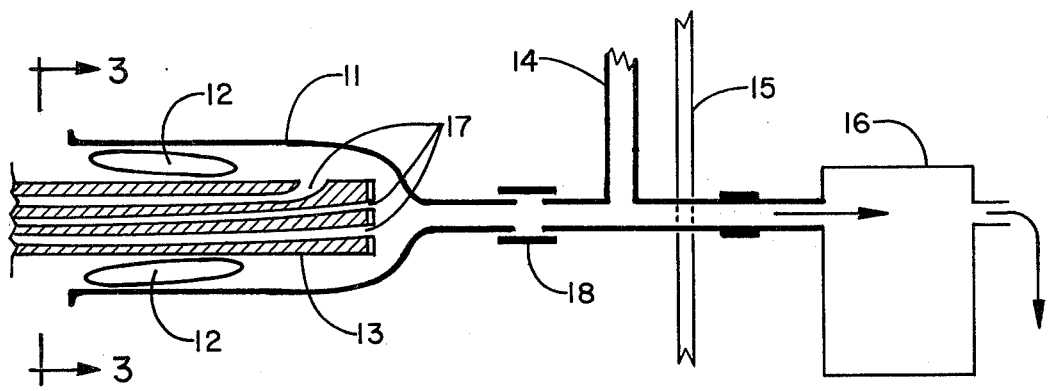
FIG. 1 is a view in section of one embodiment of the present invention connected to apparatus for sterilizing medical instruments.

Referring to FIG. 1, which is a view in section of the device of the present invention connected to apparatus for sterilizing medical instruments and the like, there is shown a funnel-like means 11, having a cylindrical cross-section. Inflatable means 12 is maintained within funnel-like means 11 by any method appropriate, such as adhering, forming means 11 and 12 integrally, or by other methods well known to those skilled in the art, which methods form no part of this disclosure.

Endoscope or other instrument 13 is shown disposed within inflatable means 12; tubes or lumens 17 of instrument 13 are those which are difficult to sterilize with devices of the existing art. Funnel-like means 11 is connected to T-tube 14 through connector 18; one arm of T-tube 14 passes through a gas-tight seal through wall 15 of the sterilizing apparatus, and is connected to vacuum pump 16. On activation of pump 16, gas within the sterilizing apparatus is exhausted, reducing the pressure to below atmospheric, and causing a gas flow generally through lumens 17 and T-tube 14.

Inflatable means 12 is preferably a sealed envelope with a gas contained therein, wherein the term "gas" as used herein is defined as any substance having a vapor pressure equal to or greater than the normal ambient pressure of the sterilizing apparatus at about 20 C. Means 12 is necessarily impervious to the gas, and sufficiently flexible to permit the interior walls thereof to expand with decreasing apparatus pressure.

Figure 2:
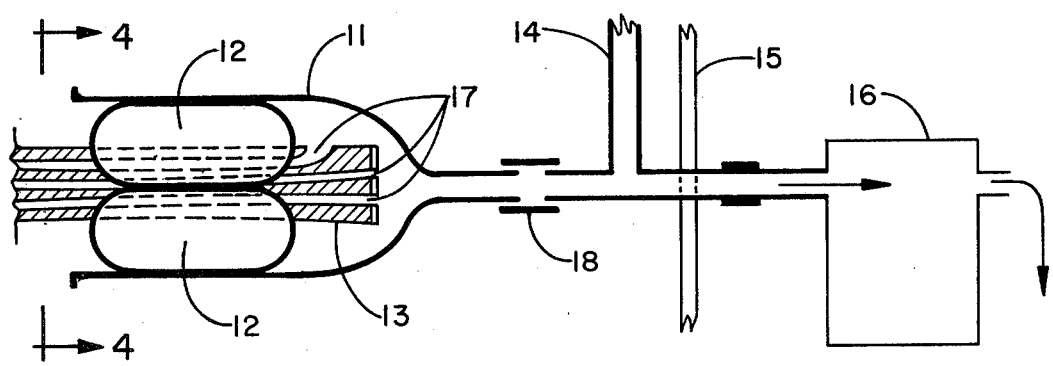
FIG. 2 is a view similar to FIG. 1, showing the invention in an inflated state.

FIG. 2 shows a view of the funnel-like means 11 with inflatable means 12 in the expanded state due to the expansion of the gas contained therewithin as a result of decreased pressure in the sterilizing apparatus. Inflatable means 12 is shown as a toroidal shape, having expanded to surround and grip tightly the medical or other device 13 tightly near the end where lumens 17 terminate in the device. Because of the necessity for the sterilizing gas to contact all interior and exterior surfaces, the surface of inflatable means 12 which comes into contact with the device to be sterilized is preferably provided with, e.g., a plurality of fibers whose ends contact the device, or with extensible paper, fabric or other substance which is itself permeable to the gas.

Figure 3:
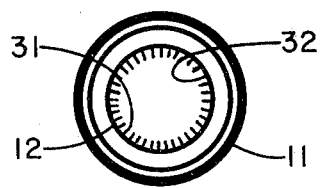
FIG. 3 is a transverse sectional view of the holder of the present invention in the relaxed state.

FIG. 3 is a view in section taken along lines 3—3 of FIG. 1, showing the medical or other device 13 disposed in funnel-like means 11, juxtaposed in inflatable means 12. Fibers 31 are shown as protruding at substantially right angles to the interior surface 32 of inflatable means 12.

Figure 4:
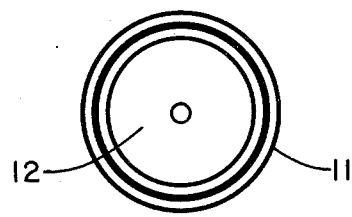
FIG. 4 is a transverse sectional view of the inflated holder.

FIG. 4 is a view in section taken along lines 4—4 of FIG. 2, showing inflatable means 12 in the inflated state.

FIG. 5 shows another embodiment of the invention in a sectional side view. Funnel-like means 51 has a conical configuration, as does inflatable means 52. FIG. 6 shows the same embodiment with means 52 inflated. This embodiment permits means 52 to grip instrument 13 securely, irrespective of irregular exterior configuration, while permitting the gripping action to be gentle enough to avoid damage to delicate parts, as end 63 of means 52 is free to expand away from instrument 13 to avoid extreme pressure.

In FIG. 7, funnel-like device 71 has recesses 73 into which inflatable means 72 fit. In this embodiment, a plurality of inflatable means are maintained in the funnel-like device.

FIG. 8 shows an end view of another embodiment of the invention. Funnel-like device 81 has a slot 83 into which fit the ends of inflatable means 82. Inflatable means 82 can alternatively be disposed in a linear fashion, as shown in FIG. 9, where a plurality of such means are shown in funnel-like means 91, which has a rectangular or box configuration. In this embodiment, a number of devices 13 could be inserted between adjacent pairs of inflatable means 82, to effect simultaneous treatment. On evacuation of the sterilizing apparatus, means 82 become inflated, causing objects therebetween to be held firmly, in a manner similar to the embodiments hereinabove described.

In many sterilization processes, particularly those involving ethylene oxide vapor, after the materials to be sterilized are placed in the sterilizing chamber, a vacuum is generated within the chamber by activating a pump, while preventing air from entering the chamber.

During this state, the inflatable holder grips one end of the endoscope, catheter, or similar instrument. In particular, all the openings of the small narrow tubes which are to be exposed to gas are contained within the holder. It is a particular feature of the sterilizer which is described in my copending application Ser. No. 212,972 that when the chamber pressure has been reduced by means of pump 16 to a predetermined level, a solenoid valve situated beyond the pump outlet diverts the outflow of air or other gas from the sterilizer vent and directs it by an external circuit back into the sterilizer. Thus, the chamber atmosphere is recirculated. By proper selection of the inside diameters of the T-tube 14, relative to the inside diameters of the fine tubules 17, a portion of the recirculating atmosphere is made to pass through the tubules.

The design of the sterilizer referred to in application Ser. No. 212,972 is such that immediately after the recirculation starts, the sterilizing gas is admitted to the chamber automatically, and as recirculation continues, the sterilizing vapor-air mixture is drawn through all the orifices connected to the inflatable holder.

As the gas is admitted, the pressure rises in the chamber; depending upon pre-arranged parameters, the final chamber pressure may be slightly lower than, equal to, or higher than atmospheric pressure. In all cases, however, the inflatable holder, being made of elastomeric material, will deflate and relax its hold upon the instrument. However, a sterilizing atmosphere has already been drawn into the lumens of the instruments and no further recirculation of gas through them is necessary to effect sterilization. When the inflatable holder is deflated, that portion of recirculating gas which is entering T-tube 14 passes over the exterior of the instrument as it rests loosely in the holder, for the entire sterilization period. Thus, both inner and outer surfaces are exposed to gas, whether before, during or after evacuation of the sterilizer.

At the conclusion of the sterilization period, many gas sterilizers incorporate gas-purging and aeration steps. At the beginning of this step, the vacuumpump solenoid directs chamber air out through a vent to the exterior. During the first few minutes of this purging step, the air inlet to the sterilizer is not opened, and so a vacuum is drawn in the chamber. The purpose of this is to be certain that when the air inlet valve from the room to the chamber is opened, the gas will not flow from chamber to the exterior. This vacuum once again inflates the holder. The air-inlet valve from the room is now opened very slightly, so the chamber is still at a pressure sufficiently lower than atmospheric to keep the holder inflated, and diluting air enters the chamber, to be discharged by the pump through the vent. This limited flushing serves to remove the sterilizing gas atmosphere from inside the tubes. When this has been accomplished, the air inlet valve is opened wide, which produces an effective equivalence in pressure between chamber and outside atmosphere, and causes the holder to deflate. The air now enters and leaves the chamber freely, and can contact all the outer surfaces of the instrument to aerate it and desorb any absorbed sterilizing gas. The air can pass over all of the exterior of the instrument, which is now lying loosely within the deflated holder.

In general, this invention discloses inflatable structures which act as holders for objects with long and narrow tubulatures, and which seal the objects within a confining structure in a gentle but positive manner, so that a fluid may be sucked through the small tubes. This is accomplished in a chamber in which a pressure lower than atmospheric is generated. Once the chamber atmosphere has traversed the tubes, the chamber pressure is returned to nearly equal the atmospheric pressure. The holder then deflates and the chamber atmosphere can contact the entire outer surface of the object.

Modifications, changes and improvements to the present forms of the invention herein disclosed, described and illustrated may occur to those skilled in the art who come to understand the principles and precepts thereof. Accordingly, the scope of the patent to be issued hereon should not be limited to the particular embodiments of the invention set forth herein, but rather should be limited by the advance by which the invention has promoted the art.

I claim:

1. A device for holding medical instruments during sterilization comprising in combination a gas-tight sterilizing apparatus and an inflatable holder, said holder comprising sealed inflatable means maintained in a rigid holder within said sterilizing apparatus, said inflatable means being in a relaxed, non-rigid state at ambient pressure within said sterilizing apparatus thereby permitting the surfaces of said instruments to be contacted by a sterilizing medium and in an inflated state, for securely holding said instruments, under conditions of reduced pressure within said sterilizing apparatus.

2. The device of claim 1 wherein said inflatable means comprises a toroidal shape.

3. The device of claim 1 wherein said inflatable means is conical in shape.

4. The device of claim 1 comprising a plurality of said inflatable means.

5. The device of claim 1 wherein said rigid holder and said inflatable means comprise an integral unit.

6. The device of claim 1 wherein said inflatable means comprises a linear shape.

7. The device of claim 6 comprising a plurality of said linearly shaped inflatable means.

* * * * *